United States Patent [19]

Shaw et al.

[11] 4,114,604

[45] Sep. 19, 1978

[54] CATHETER OXIMETER APPARATUS AND METHOD

[76] Inventors: Robert F. Shaw, 135 Willowbrook Dr., Portola Valley, Calif. 94025; John M. Sperinde, 6582 Canterbery Ct., San Jose, Calif. 95129

[21] Appl. No.: 733,278

[22] Filed: Oct. 18, 1976

[51] Int. Cl.² .............................................. G01N 33/16
[52] U.S. Cl. ...................................... 128/2 L; 356/41
[58] Field of Search .................... 128/2 L, 2.05 F; 356/40, 41

[56] References Cited

U.S. PATENT DOCUMENTS

| | | | |
|---|---|---|---|
| 3,638,640 | 2/1972 | Shaw | 128/2 R |
| 3,647,299 | 3/1972 | Lavallee | 356/41 |
| 3,677,648 | 7/1972 | Dorsch | 356/40 |
| 3,822,695 | 7/1974 | Takayama | 128/2 L |
| 3,825,342 | 7/1974 | Lubbers et al. | 356/41 |
| 3,847,483 | 11/1974 | Shaw et al. | 356/41 |

OTHER PUBLICATIONS

Borgnis, F. E., "A New Reflexion Oximeter", Biomedical Technik, vol. 18, No. 4, Aug. 1973, pp. 142–147.

Primary Examiner—Robert W. Michell
Assistant Examiner—Francis J. Jaworski
Attorney, Agent, or Firm—Lyon & Lyon

[57] ABSTRACT

An improved catheter oximeter operates on radiation at three or more different wavelengths applied to and scattered back from blood under test to provide an indication of oxygen saturation and is considerably less sensitive to accuracy-degrading variations in the blood and its environment and in the oximeter measuring system.

19 Claims, 4 Drawing Figures

CATHETER OXIMETER APPARATUS AND METHOD

RELATED APPLICATIONS

The subject matter of this application is related to the subject matter of application Ser. No. 733,279 entitled "Improved Optical Catheter Not Requiring Individual Calibration" filed on Oct. 18, 1976 and application Ser. No. 733,280 entitled "Sterilizable Disposable Optical Scattering Reference Medium" filed Oct. 18, 1976 on the disclosures of which are incorporated herein by reference.

BACKGROUND OF THE INVENTION

Blood oxygen saturation is the relative amount of oxygenated hemoglobin in all of the hemoglobin present in the blood stream. This hemoglobin is packaged in biconcave discs of approximately 10 micrometers diameter which commonly occur with a density of approximately five million red blood cells per cubic millimeter. The red blood cells both scatter and transmit the incident radiant energy. The differential absorption by oxygenated and non-oxygenated hemoglobin of the radiant energy transmitted through the red blood cells furnishes the basis for the oxygen saturation measurement. In conventional catheter oximetry, the radiation wavebands being used to measure the blood at a measurement site in vivo are conducted from the oximeter device to the position of interest within the flowing blood stream by means of an optical catheter including light-transmitting and light-receiving fiberoptic light guides. The receiving fiberoptic light guide for conducting light from the blood stream back to a photodetector in the oximeter device commonly has its inlet aperture coplanar with the outlet aperture of the transmitting fiberoptic light guide. Thus, only back-scattered light is available for measurement, and this represents only a very small fraction of the total light transmitted to the measurement site. The light scatterers present about the measurement site thus act as sources of light for the receiving optical light guide. Consequently, the intensity of the light scattered back to the receiving optical light guide is influenced by variations in the number of scatterers, their location, size, shape and orientation as well as by the differential absorption by oxyhemoglobin and hemoglobin.

The blood under test flows within a vessel of interest in a pulsatile manner, and the catheter tip thus moves in an uncontrolled manner with respect to the blood vessel walls. Whenever a blood vessel wall appears in the near field of the catheter tip, this has the effect of introducing a very large array of tightly packed backscatterers into the measurement system. This introduces a significant change in the distribution and number of scatterers, which has a substantial and wavelength-dependent effect upon intensities of light received by the receiving fiber as a function of transmission through hemoglobin and oxyhemoglobin (which have wavelength-dependent radiation absorption characteristics).

Certain known catheter-type oximeter devices respond to the intensities of such back-scattered radiation at only two different wavelengths. Oximeter devices of this type are disclosed in the literature (see, for example, U.S. Pat. No. 3,847,483 issued to R. F. Shaw, et al, on Nov. 12, 1974). In these known devices, the radiation intensities measured at two wavelengths provide an indication of oxygen saturation according to the relationship:

$$OS = \frac{A_0 + A_1 I_1 + A_2 I_2}{B_0 + B_1 I_1 + B_2 I_2} \qquad (Eq. 1)$$

where $I_1$ and $I_2$ are the light intensities measured at wavelengths $\lambda_1$ and $\lambda_2$, respectively.

It should be noted that if both the numerator and denominator of Equation 1 are divided by one of the light intensity measurements, i.e., $I_1$, the resultant expression is $$OS = \frac{\frac{A_0}{I_1} + A_1 + A_2(\frac{I_2}{I_1})}{\frac{B_0}{I_1} + B_1 + B_2(\frac{I_2}{I_1})}. \qquad (Eq. 2)$$

Because the OS measurement thus made according to the prior art remains a function not only of the ratio of light intensities but of individual light intensities as well, variations in such phenomena as blood flow velocity, hematocrit, pH, $pCO_2$, and the like (which are multiplicative and wavelength dependent), can introduce errors into the oxygen saturation measurement thus obtained.

The apparatus of the aforecited patent exhibits greater immunity to such sources of error as variations in blood flow velocities, hematocrits, and hemoglobin concentrations than apparatus previously known. However, even greater immunity is desirable to such sources of error in applications requiring high-accuracy in vivo measurements of oxygen saturation. In particular, less sensitivity to proximity of the catheter tip to blood vessel walls is preferable. In addition, a detectable influence upon measurement accuracy due to variations in hematocrit, flow velocity, pH, $pCO_2$, osmolarity, and variations in the transmissivity of the optical fibers is also present, and, to some extent, error also can result from a linear characterization of nonlinear phenomena in the prior art.

SUMMARY OF THE INVENTION

In accordance with the present invention, oxygen saturation is measured as a function only of the ratios of light intensities at selected wavebands, and thus, multiplicative wavelength-independent variations do not degrade the measurement accuracies.

Since the relationship between oxygen saturation and the ratio of light intensities is not quite linear, the apparatus of the present invention uses piecewise linear relationships or nonlinear relationships to measure oxygen saturation over a wide dynamic range of values.

Also, since many of the above noted phenomena which are present at the measurement site within a blood vessel may vary, both multiplicative and additive aspects of the optical measurement are considered in the present invention which provides an oxygen saturation measurement in accordance with one of the following equations:

$$OS = \frac{A_0 + A_1(\frac{I_1}{I_2}) + A_2(\frac{I_3}{I_2})}{B_0 + B_1(\frac{I_1}{I_2}) + B_2(\frac{I_3}{I_2})} \qquad (Eq. 3)$$

$$OS = \frac{A_0 + A_1(\frac{I_1}{I_2}) + A_2(\frac{I_1}{I_2})^2 + A_3(\frac{I_3}{I_2})}{B_0 + B_1(\frac{I_1}{I_2}) + B_2(\frac{I_1}{I_2})^2 + B_3(\frac{I_3}{I_2})} \quad \text{(Eq. 4)}$$

$$OS = \frac{\Sigma A_j R_j^i}{\Sigma B_j R_j^i} \quad \text{(Eq. 5)}$$

where $A_0$, $A_1$, $A_2$, $A_3$, and $A_i$ are weighting factors or coefficients, $B_0$, $B_1$, $B_2$ and $B_3$, and $B_i$ are weighting factors or coefficients, and $I_1$, $I_2$, and $I_3$ are light intensities measured at wavelengths $\lambda_1$, $\lambda_2$ and $\lambda_3$, respectively, each normalized with respect to a reference light intensity measurement, and $R_i$ is the ratio of the normalized light intensities measured at the three different wavelengths.

It should be noted that oxygen saturation measured in accordance with Equation 3 is a function of the ratios of light intensity measurements which is useful for determining oxygen saturation over a narrow range of values. However, to compensate for the non-linearities of the underlying phenomena which have significant effect over a wide dynamic range of values, Equation 3 can be augmented by adding terms proportional to the square of a ratio of light intensities, as indicated in Equation 4. In addition, these equations can be further extended to the general expression indicated in Equation 5.

In the present invention, at least three wavebands illuminate the blood at the measurement site in vivo and furnish the two ratios of intensities required to determine oxygen saturation at the measurement site. These wavebands have been selected to minimize errors introduced into the oxygen saturation measurement by wavelength-dependent variations in the phenomena noted above. The coefficients of the terms in Equations 3 and 4 are selected such that the partial derivative of the calculated oxygen saturation with respect to one of the ratios is approximately zero near the lower extreme of the range of oxygen saturation values of physiologic interest, and the partial derivative of calculated oxygen saturation with respect to the other ratio in Equations 3 and 4 is approximately zero near the high extreme of the range of oxygen saturation values of physiologic interest. Also, the coefficients of the terms in each of these equations may be selected to satisfy the constraint that the sum of all numerator coefficients is approximately zero and the sum of all denominator coefficients is approximately zero.

DESCRIPTION OF THE PREFERRED EMBODIMENT

Figure 1:
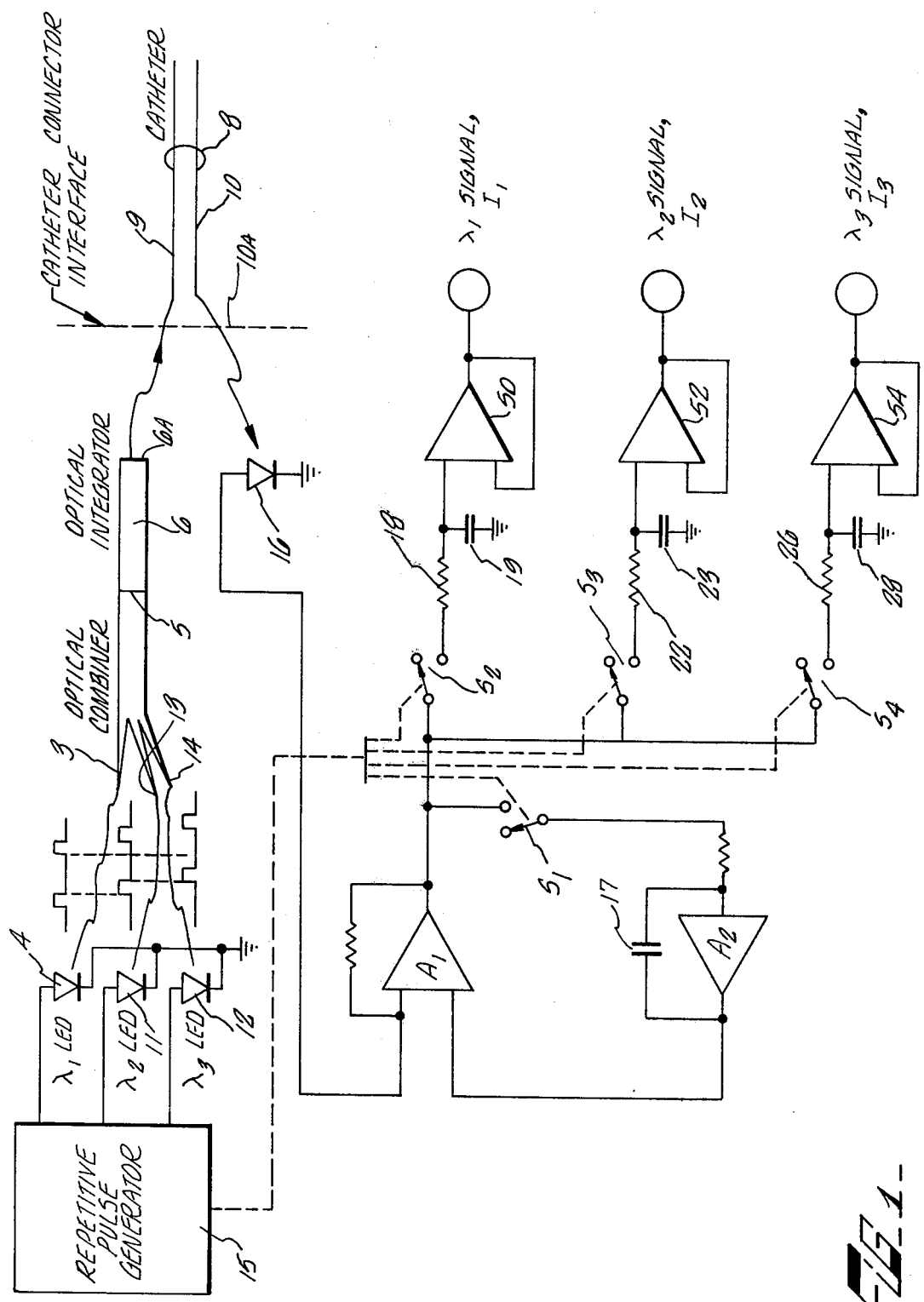
FIG. 1 is a pictorial diagram of one embodiment of the present invention.

Referring now to FIG. 1, there is a shown a portion of a schematic diagram including radiation source means, optical combiner and integrator means, catheter, detector, and signal processing means according to one embodiment of the present invention. The radiation source means includes three light emitting diodes 11, 12, and 4 which are arranged to alternately irradiate three branches 13, 14 and 3 of a fiber optic guide. The light emitting diodes 11, 12, and 4 are each alternately energized typically for about 25 percent of the operating cycle, in non-overlapping temporal relationship by the pulse generator 15. The operating cycle computes three periods of sequential energizing of the light emitting diodes followed by a period in which none of the light emitting diodes 11 or 12 or 4 is energized. Each operating cycle thus comprises four periods and an example rate is two hundred and fifty such cycles per second.

Light emitting diodes 4, 11, and 12 emit radiation at wavelengths $\lambda_1$, $\lambda_2$, and $\lambda_3$, respectively. This radiation is collected by fiber optic guides 13, 14, and 3 which may contain one or more fibers that are physically combined into a bundle having minimum end cross section 5 of about the same shape and size as the optical integrator 6.

The optical integrator 6 is disposed continuous to the surface 5 and is a single light guide of approximately the same size as end 5 and has a square cross section and a large ratio of length-to-lateral dimension to assure that spatially-separated radiation at surface 5 is uniformly distributed over exit aperture 6A. Consequently, a single transmitting fiber 9 or a bundle of transmitting fibers coupled to aperture 6A thus receives an amount of radiation at each of the three wavelengths which is not changed significantly by small transverse misalignments which might occur between optical integrator 6 and the transmitting fiber 9.

Only one efferent fiber 9 of catheter 8 is required to transmit the radiation at the three wavelengths to blood at the distal end of the catheter 8. The transmitting light guide 9 and the receiving light guide 10 of catheter 8 may each consist of only a single optical fiber which greatly simplifies the construction of the catheter and makes possible a low-cost disposable catheter which can be coupled to the measuring equipment at an interface connector 10A.

When the distal tip of the catheter 8 is immersed in blood in a blood vessel or other blood-confining container, radiation from the transmitting light guide 9 at each of the three wavelengths is selectively absorbed and scattered by the red cells, and a portion of the backscattered radiation enters the aperture at the distal tip of the receiving light guide 10. At the proximal end of the catheter 8, the aperture of light guide 10 is optically coupled to the radiation detector 16 so that substantially all of the radiation exiting from the light guide 10 impinges upon the active area of the detector 16.

Radiation signals detected by 16 are amplified by the detector amplifier A1. During the times that none of the light emitting diodes 11 or 12 or 4 is emitting radiation, switch S1 is closed by a signal from the pulse generator 15. This forms a closed loop servo system between amplifiers A1 and A2 which establishes a bias voltage on amplifier A1 that adjusts its output voltage to zero.

During the times that switch S1 is open this zero-correcting bias voltage for amplifier A1 is maintained by the charge stored in the operationally-connected feedback capacitor 17. This action assures that the output voltage of the detector amplifier A1 will be zero when the detector 16 is receiving no back-scattered radiation and thereby compensates for amplifier drift and spurious outputs from the detector 16.

During the time that diode 4 is radiating, switch S2 is closed by a signal from the pulse generator 15 and the signal voltage at the output of the detector amplifier A1 (due to the received radiation from the light emitting diodes that is back-scattered by the blood) is applied to the filter consisting of resistor 18 and capacitor 19. The action of switch S2, resistor 17 and capacitor 19, thus produces an average signal voltage across capacitor 19 which is representative of the intensity of the radiation at the wavelength produced by light emitting diode 4 and backscattered from the blood under test. This average signal voltage is amplified by amplifier 50 to provide a continuous output voltage that is directly related to the intensity of radiation at the wavelength $\lambda_1$ produced by light emitting diode 4 and backscattered from blood under test.

Similarly, switch S3, resistor 22, and capacitor 23 and the amplifier 52 operate in substantially the same manner during the portion of the cycle while light emitting diode 11 is energized to produce a continuous voltage at the output of amplifier 52 that is directly related to the intensity of radiation at the wavelength $\lambda_2$ produced by light emitting diode 11 and backscattered from the blood under test. In the same manner, switch S4 and the resistor 26 and capacitor 28 and amplifier 54 operate during a portion of the cycle while light emitting diode 12 is energized to produce a continuous voltage at the output of amplifier 54 that is directly related to the intensity of radiation of the wavelength $\lambda_3$ produced by the light emitting diode 12 and backscattered from the blood under test.

Figure 2:
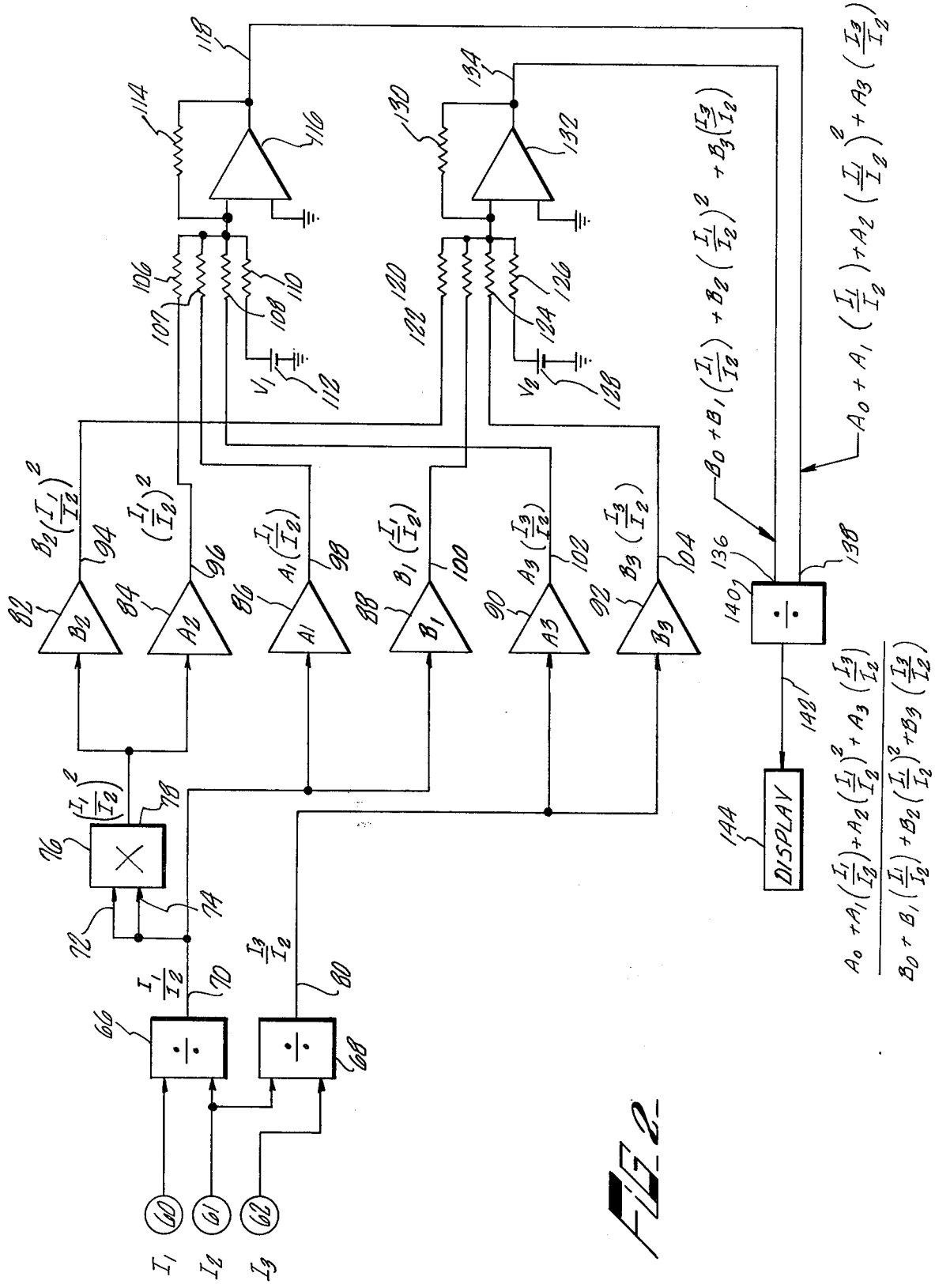
FIG. 2 is a schematic diagram of one embodiment of a circuit for producing the oxygen saturation output as a function of the ratios of radiation intensities at three wavelengths.

Referring now to FIG. 2, there is shown a block diagram of a signal processor according to one embodiment of the present invention. The output signals from amplifiers 50, 52 and 54 of FIG. 1 are applied to terminals 60, 61 and 62, respectively, of FIG. 2.

Signals appearing on terminals 60 and 61 are applied to a dividing circuit 66 which produces an output 70 that is equal to the ratio of $I_1/I_2$. The signal at output 70 is applied to the inputs 72 and 74 of a multiplying circuit 76 which produces an output 78 that is equal to $(I_1/I_2)^2$.

The signals appearing on terminals 61 and 62 are also applied to a dividing circuit 68 which produces an output 80 that is equal to the ratio of $I_3/I_2$.

Amplifier 82 operates on the output signal 78 with the appropriate gain and sign, $B_2$, to produce a signal at output 94 which equals $B_2(I_1/I_2)^2$. Similarly, amplifiers 84, 86, 88, 90, and 92 operate on their respective inputs with appropriate gain and sign to produce output signals which are representative of weighted intensity ratios, as shown.

The amplifier outputs 96, 98, and 102 are applied to a summing amplifier circuit 116 which produces output 118 that is equal to:

$$A_0 + A_1(I_1/I_2) + A_2(I_1/I_2)^2 + A_3(I_3/I_2) \quad \text{(Eq. 6)}$$

The voltage source 112, along with the resistors 110 and 114, produce the $A_0$ term in the output 118.

Similarly, the summing amplifier circuit 132 produces an output 134 that is equal to:

$$B_0 + B_1(I_1/I_2) + B_2(I_1/I_2)^2 + B_3(I_3/I_2) \quad \text{(Eq. 7)}$$

The voltage source 128 along with resistors 126 and 130, produce the $B_0$ term in the output 134. The resultant signals at 118 and 134 are applied to circuit 140 which takes the ratio of the signal at the input 136 and 138 and produces output 142 which is indicative of the oxygen saturation of the blood under test. The oxygen saturation, displayed on a suitable display means 144 is thus equal to:

$$OS = \frac{A_0 + A_1(\frac{I_1}{I_2}) + A_2(\frac{I_1}{I_2})^2 + A_3(\frac{I_3}{I_2})}{B_0 + B_1(\frac{I_1}{I_2}) + B_2(\frac{I_1}{I_2})^2 + B_3(\frac{I_3}{I_2})} \quad \text{(Eq. 8)}$$

Figure 3:
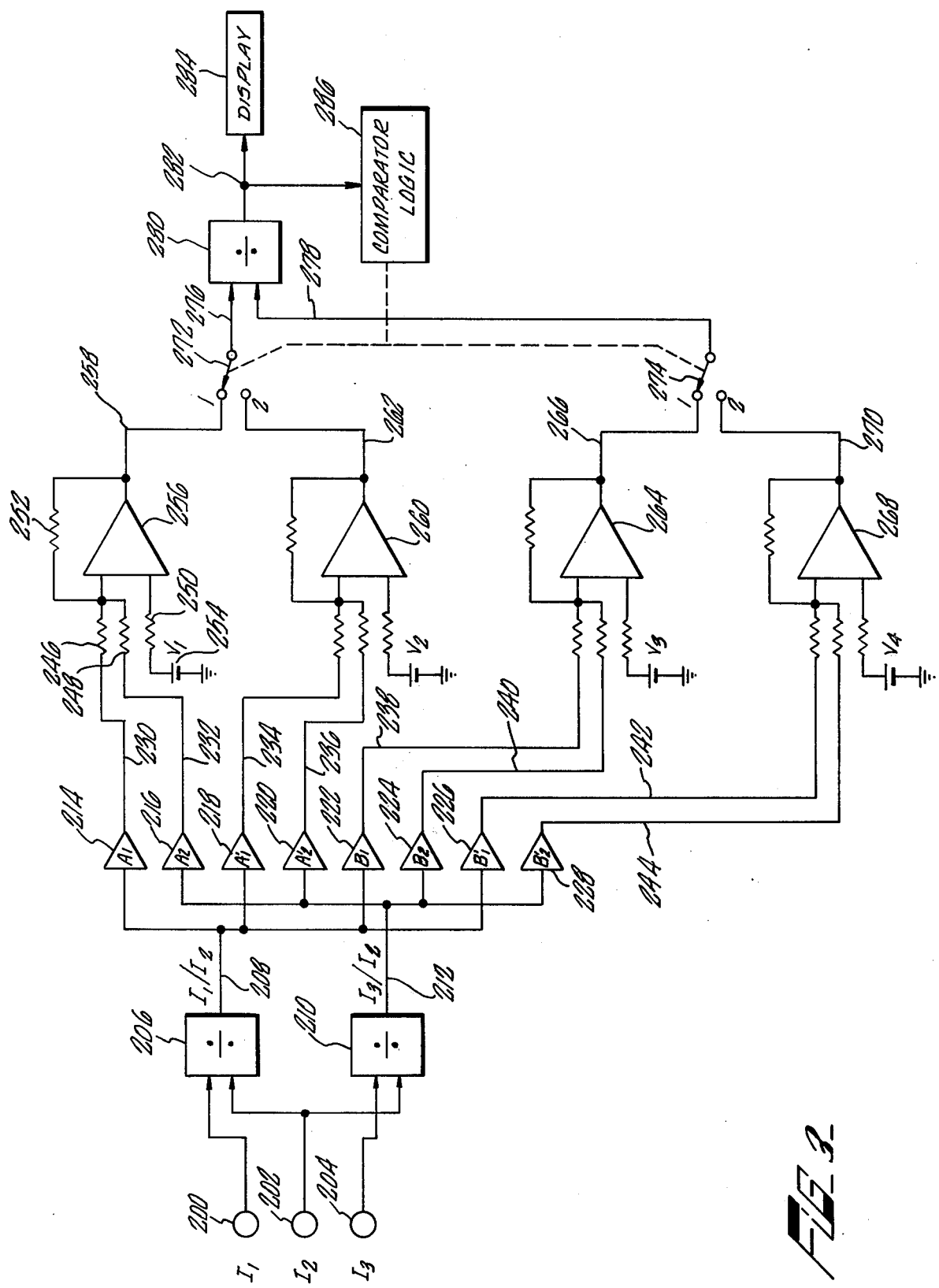
FIG. 3 is a schematic diagram of another embodiment of a circuit for producing the oxygen saturation output as a function of the ratios of radiation intensities at three wavelengths.

Referring to FIG. 3 there is shown a block diagram of the signal processor according to another embodiment of the present invention. The output signals from amplifiers 50, 52 and 54 of FIG. 1 are applied to terminals 200, 202, and 204, respectively, of FIG. 3.

Signals from 200 and 202 are applied to a dividing circuit 206 which produces an output 208 that is equal to the ratio $I_1/I_2$. Signals from 202 and 204 are applied to a dividing circuit 210 which produces an output 212 that is equal to the ratio $I_3/I_2$.

An amplifier 214 operates on the signal 208 with the appropriate gain and sign A1 to produce a signal at 230 which is equal to $A_1(I_1/I_2)$. Similarly, amplifiers 216 through 228 operate on their inputs with the appropriate gain and sign to produce the following outputs:

| Signal Line Number | Signal |
|---|---|
| 230 | $A_1(I_1/I_2)$ |
| 232 | $A_2(I_3/I_2)$ |
| 234 | $A_1'(I_1/I_2)$ |
| 236 | $A_2'(I_3/I_2)$ |
| 238 | $B_1(I_1/I_2)$ |
| 240 | $B_2(I_3/I_2)$ |
| 242 | $B_1'(I_1/I_2)$ |
| 244 | $B_2'(I_3/I_2)$ |

Signals from 230, 232, and 254 are applied to the summing amplifier 256 to produce an output at 258. With the appropriate choice of resistors 246, 248, 250, and 252, and the source 254 of voltage $V_1$, the output signal at 258 equals:

$$A_0 + A_1(I_1/I_2) + A_2(I_3/I_2). \quad \text{(Eq. 9)}$$

Similarly, the outputs of amplifiers 260, 264, and 268 will have the following form:

| Signal Line Number | Signal | |
|---|---|---|
| 262 | $A_0' + A_1'(I_1/I_2) + A_2'(I_3/I_2)$ | (Eq. 10) |
| 266 | $B_0 + B_1(I_1/I_2) + B_2(I_3/I_2)$ | (Eq. 11) |
| 268 | $B_0' + B_1'(I_1/I_2) + B_2'(I_3/I_2)$ | (Eq. 12) |

A switch 272 selects either the output 258 or 262. A switch 274 selects either the output 266 or 270. The switches 272 and 274 are synchronized to operate both in position 1 or both in position 2.

The resultant signals at 276 and 278 are applied to a circuit 280 which takes the ratio of the signals at the inputs 276 and 278 to produce the output 282 which is indicative of the oxygen saturation of the blood under test. The oxygen saturation, with switch 272 and 274 inposition 1 may be displayed on a suitable display means 284 and is equal to:

$$OS = \frac{A_0 + A_1(\frac{I_1}{I_2}) + A_2(\frac{I_3}{I_2})}{B_0 + B_1(\frac{I_1}{I_2}) + B_2(\frac{I_3}{I_2})} \quad \text{(Eq. 13)}$$

and with switches 272 and 274 in position 2, the oxygen saturation is equal to:

$$OS = \frac{A_0' + A_1'(\frac{I_1}{I_2}) + A_2'(\frac{I_3}{I_2})}{B_0' + B_1'(\frac{I_1}{I_2}) + B_2'(\frac{I_3}{I_2})} \quad \text{(Eq. 14)}$$

The comparator logic 286 controls the position of switches 272 and 274. If the OS signal at 282 is above an appropriate value, say 85%, the switches 272 and 274 are in position 1. If the OS signal at 182 is below the appropriate value, the switches 272 and 274 are in position 2. The arrangement allows the appropriate choice of the coefficients, $A_1$, $A_2$, $A_3$, $B_1$, $B_2$, $B_3$, $A_1'$, $A_2'$, $A_3'$, $B_1'$, $B_2'$, and $B_3'$, to maximize the accuracy of the system in a piecewise manner over a wide range of oxygen saturation values.

In operation, the apparatus of the present invention uses a set of three wavebands at approximately 670 nanometers, 700 nanometers, and 800 nanometers. These wavelengths were selected on the basis of a large quantity of data taken from in-vitro studies with heart-lung machines and in-vivo studies conducted in anesthetized experimental animals, human volunteers, and clinical patients undergoing surgery and intensive care.

Figure 4:
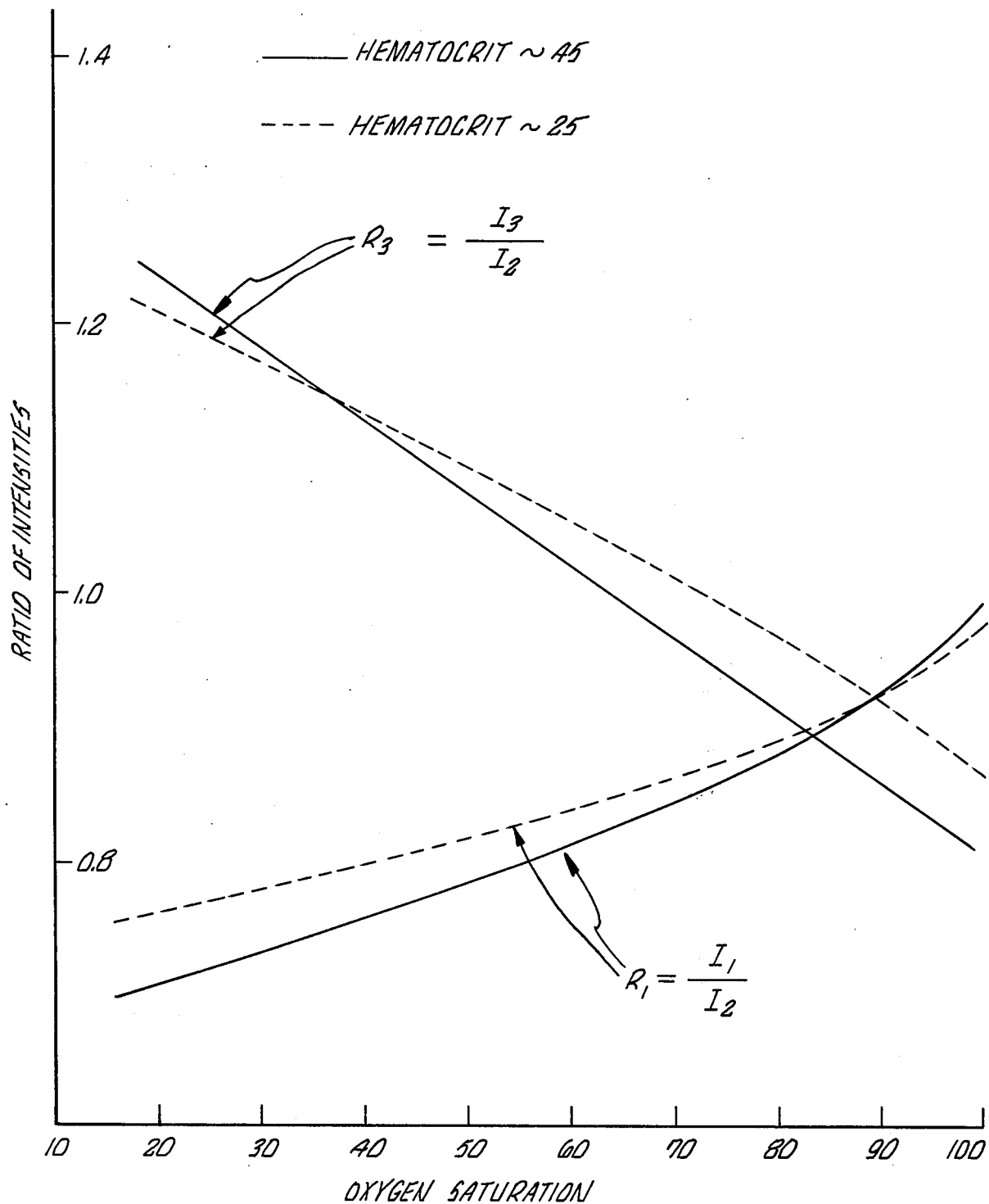
FIG. 4 is a graph showing the effect of a variation in a typical wavelength-dependent characteristic of the blood on the relationship between oxygen saturation values and the ratios of intensities of detected radiation at three different wavelengths.

For each pair of wavelengths selected, it is possible to plot the ratio of reflectance as a function of oxygen saturation with a particular physiologic variable as a parameter. The graph of FIG. 4 is a plot of independently-measured oxygen saturation versus the ratio of reflectances at 670 nm and 700 nm ($R_1$) and versus the ratio of reflectances at 800 nm and 700 nm ($R_3$) for two hematocrit values 25 and 45 which are near the extremes of the range of values of interest. From the graph of FIG. 4, it can be seen that $R_3$ is independent of hematocrit at approximaterly 36% oxygen saturation and varies highly with hematocrit in the upper regions of the oxygen saturation range. Similarly, $R_1$ is independent of hematocrit at an oxygen saturation of approximately 90% oxygen saturation and varies widely with hematocrit in the lower regions of interest of the oxygen saturation range.

It is possible to graph the relationship between experimentally determined oxygen saturation and the ratios of many different wavelengths of interest for the large number of significant physiologic parameters whose variation may degrade accuracy of oxygen saturation measurement. From an examination of many such ratios and the variations in many such physiologic parameters, it is possible to select appropriate wavelengths whose ratios of intensities will minimize the cumulative error of the various parameters studied, near the extremes of the oxygen saturation range of interest.

In order to make the computed oxygen saturation most heavily dependent upon that light intensity ratio which exhibits minimum variation for a given parameter (such as hematocrit as in the graph of FIG. 4) in a particular oxygen saturation range (such as $R_3$ around 36% OS, and $R_1$ around 85% OS as seen in FIG. 4), the weighting factors or coefficients of Equations 3, 4, and 5 should be selected such that the differential of computed oxygen saturation with respect to the other ratio is zero where the variation of the first ratio is at a minimum. From FIG. 4 it can be seen that at an oxygen saturation range of about 25 to 45% for example, the ratio $R_3$ exhibits a minimal variation and the ratio $R_1$ exhibits a large variation, on the other hand, around 75 to 95% oxygen saturation the variation of $R_1$ is minimal and that of $R_3$ is large. Weighting in the direction of last variation or error thus eliminates the poor ratio. Therefore, in the range of 25 to 45% OS the derivative of oxygen saturation with respect to $R_1$ should be approximately zero, and in the range of 75 to 95% OS the derivative of oxygen saturation with respect to $R_3$ should be approximately zero. This constraint upon the selection of weighting factors tends to minimize the errors in oxygen saturation measurement introduced by variations in wavelength-dependent characteristics, other than oxygen saturation, of blood under test.

By further selecting the weighting factors to cause the sum of all weighting factors in the numerator to approximate zero and the sum of all weighting factors in the denominator to approximate zero, the errors in oxygen saturation measurement introduced by variations in additive characteristics of blood under test are also minimized. This constraint can only be operative if three or more radiation wavebands are used.

Therefore, the present invention uses the ratios of light intensities back-scattered from blood under test of at least three different wavebands to determine oxygen saturation of blood in vivo. Also, the wavebands at which the measurements are made are selected to yield an indication of oxygen saturation which is relatively insensitive to variations in wavelength-dependent aspects, multiplicative aspects, and additive aspects of the measurement system.

We claim:
1. Apparatus for determining oxygen saturation of blood comprising:
    source means for producing electro-magnetic radiation at first, second and third radiation wavelengths;
    means coupled to the source means for supplying the radiation therefrom to blood under test with incident intensities at the respective wavelengths;
    detector means disposed to receive radiation from the blood under test altered from the incident intensities of the respective wavelengths by the optical properties of the blood under test for producing signals representative of the intensities of the radiation received thereby at the respective wavelengths;
    circuit means coupled to the detector means for producing a first output representative of the ratio of a first pair of the signals from said detector means, and for producing a second output representative of the ratio of a second pair of the signals from said detector means, the wavelengths of the radiation from said source means being such that the first ratio is independent of physiological changes of the sample blood other than oxygen saturation at a first oxygen saturation level and the second ratio is independent of physiological changes other than oxygen saturation at a second oxygen saturation level; and first means coupled to the circuit means for receiving the first and second outputs of said circuit means and applying selected coefficients thereto to minimize the effect of varying physiological characteristics of the blood under test other than oxygen saturation, said first means producing an output representative of the algebraic combination of selectively weighted first and second outputs of said circuit means; and second means coupled to the circuit means for receiving the first and second outputs of said circuit means and applying selected coefficients thereto to minimize the effect of varying physiological characteristics of the blood under test other than oxygen saturation, said second means producing an output representative of the algebraic combination of selectively weighted first and second outputs of said circuit means; and means coupled to the first and second means for receiving the outputs therefrom and producing an output manifestation of the ratio of the outputs from the first and second means.

2. Apparatus as in claim 1 wherein said first and second means produce said outputs representing the polynomials $A_0 + A_1(I_1/I_2) + A_2(I_3/I_2)$ and $B_0 + B_1(I_1/I_2) + B_2(I_3/I_2)$ respectively where A and B coefficients are selectively weighted.

3. Apparatus as in claim 1 wherein the first wavelength is approximately 670 nanometers, the second wavelength is approximately 700 nanometers and the third wavelength is approximately 800 nanometers.

4. Apparatus for determining oxygen saturation of blood comprising:
source means for producing electro-magnetic radiation at first, second and third radiation wavelengths;
means coupled to the source means for supplying the radiation therefrom to blood under test with incident intensities at the respective wavelengths;
detector means disposed to receive radiation from the blood under test altered from the incident intensities of the respective wavelengths by the optical properties of the blood under test for producing signals representative of the intensities of the radiation received thereby at the respective wavelengths;
circuit means coupled to the detector means for producing a first output representative of the ratio of a first pair of the signals from said detector means, and for producing a second output representative of the ratio of a second pair of the signals from said detector means; and
first means coupled to the circuit means for producing an output representative of the algebraic combination of selectively weighted first and second outputs and square of one of the first and second outputs;
second means coupled to the circuit means for producing an output representative of the algebraic combination of selectively weighted first and second outputs and square of one of said first and second outputs; and
means coupled to the first and second means and responsive to said outputs therefrom for producing an output manifestation of the ratio of said outputs.

5. Apparatus as in claim 4 wherein said first and second means produce said outputs representative additionally of algebraic combinations with selectively weighted reference outputs.

6. Apparatus for determining oxygen saturation of blood comprising:
source means for producing electro-magnetic radiation at a plurality of radiation wavelengths;
means coupled to the source means for supplying the radiation therefrom to blood under test with incident intensities at the respective wavelengths;
detector means disposed to receive radiation from the blood under test altered from the incident intensities of the respective wavelengths by the optical properties of the blood under test for producing signals representative of the intensities of the radiation received thereby at the respective wavelengths;
circuit means coupled to the detector means for producing a plurality of outputs each representative of the ratio of a respective pair of the signals from said detector means;
first means coupled to the circuit means for producing corresponding resultant signals from at least one output multiplied in value by an output a selected number of times and for producing an output representative of the sum of all selectively weighted resultant signals; and
means coupled to the first means and responsive to said output therefrom for producing an output manifestation of oxygen saturation.

7. Apparatus as in claiam 6 wherein the output of said first means its representative additionally of algebraic combinations with selectively weighted reference outputs.

8. A method of determining oxygen saturation of blood comprising the steps of:
producing electro-magnetic radiation at three different wavebands;
coupling the radiation at each of the wavebands to blood under test;
detecting radiation at each of the wavebands received back from blood under test for producing a corresponding electrical signal representative of the intensity of the radiation received back from the blood under test at the respective waveband;
producing a first output representative of the ratio of one pair of electrical signals;
producing a second output representative of the ratio of another pair of said electrical signals;
producing third and fourth outputs representative of the algebraic combination of selectively weighted first and second outputs; and
producing an output manifestation of oxygen saturation as the ratio of said third output and said fourth output.

9. A method of determining oxygen saturation of blood comprising the steps of:
producing electro-magnetic radiation at three different wavebands;
coupling the radiation at each of the wavebands to blood under test;
detecting radiation at each of the wavebands received back from blood under test for producing a corresponding electrical signed representative of the intensity of the radiation received back from the blood under test at the respective waveband;
producing a first output representative of the ratio of one pair of said electrical signals;

producing a second output representative of the ratio of another pair of said electrical signals;

producing a third output representative of the algebraic combination of selectively weighted first output and second output and square of one of the first and second outputs;

producing a fourth output representative of the algebraic combination of selectively weighted first output and second output and square of one of the first and second outputs; and producing an output manifestation of oxygen saturation as the ratio of said third output and said fourth output.

10. A method of determining oxygen saturation of blood comprising the steps of:

producing electro-magnetic radiation at a plurality of different radiation wavelengths;

coupling the radiation at each of the respective wavelengths to the blood under test;

detecting the radiation at each of the wavelengths received back from the blood under test for producing signals representative of the intensities of the radiation received back from the blood under test at the respective wavelengths;

producing a plurality of outputs each representative of the ratio of a respective pair of said signals;

producing corresponding resultant signals from each output multiplied in value by an output a selected number of times;

producing an output representative of the sum of all selectively weighted resultant signals; and producing an output manifestation of oxygen saturation as the ratio of selected sums of resultant signals.

11. Apparatus for determining oxygen saturation of blood comprising:

source means for producing electro-magnetic radiation at first, second and third radiation wavelengths;

means coupled to the source means for supplying the radiation therefrom to blood under test with incident intensities at the respective wavelengths;

detector means disposed to receive radiation from the blood under test altered from the incident intensities of the respective wavelengths by the optical properties of the blood under test for producing signals representative of the intensities of the radiation received thereby at the respective wavelengths;

circuit means coupled to the detector means for producing a first output representative of the ratio of a first pair of the signals from said detector means, and for producing a second output representative of the ratio of a second pair of the signals from said detector means;

first means coupled to the circuit means for receiving the outputs therefrom and for weighting said outputs by applying coefficients thereto, wherein the algebraic sum of said coefficients substantially equals zero, to produce an output representative of the algebraic combination of selectively weighted first and second outputs from said circuit means; and second means coupled to the circuit means for receiving the outputs therefrom and for weighting said outputs by applying coefficients thereto, wherein the algebraic sum of said coefficients substantially equals zero, to produce an output representative of the algebraic combination of selectively weighted first and second outputs from said circuit means; and means coupled to the first and second means and responsive to said outputs therefrom for producing an output manifestation of the ratio of said outputs.

12. Apparatus for determining oxygen saturation of blood comprising:

source means for producing electro-magnetic radiation at first, second and third radiation wavelengths;

means coupled to the source means for supplying the radiation therefrom to blood under test with incident intensities at the respective wavelengths;

detector means disposed to receive radiation from the blood under test altered from the incident intensities of the respective wavelengths by the optical properties of the blood under test for producing signals representative of the intensities of the radiation received thereby at the respective wavelengths;

circuit means coupled to the detector means for producing a first output representative of the ratio of a first pair of the signals from said detector means, and for producing a second output representative of the ratio of a second pair of the signals from said detector means;

first means coupled to the circuit means for receiving the outputs therefrom and for weighting said outputs by applying coefficients thereto, wherein the algebraic sum of said coefficients substantially equals zero, to produce an output representative of the algebraic combination of selectively weighted first and second outputs and square of one of said first and second outputs from said circuit means;

second means coupled to the circuit means for receiving the outputs therefrom and for weighting said outputs by applying coefficients thereto, wherein the algebraic sum of said coefficients substantially equals zero, to produce an output representative of the algebraic combination of selectively weighted first and second outputs and square of one of said first and second outputs from said circuit means; and means coupled to the first and second means and responsive to said outputs therefrom for producing an output manifestation of the ratio of said outputs.

13. Apparatus for determining oxygen saturation of blood comprising:

source means for producing electro-magnetic radiation at a plurality of radiation wavelengths;

means coupled to the source means for supplying the radiation therefrom to blood under test with incident intensities at the respective wavelengths;

detector means disposed to receive radiation from the blood under test altered from the incident intensities of the respective wavelengths by the optical properties of the blood under test for producing signals representative of the intensities of the radiation received thereby at the respective wavelengths;

circuit means coupled to the detector means for producing a plurality of outputs each respective of the ratio of a respective pair of the signals from said detector means;

first means coupled to the circuit means for receiving the outputs therefrom, raising at least some of said outputs to selected powers of said outputs, and for weighting said outputs by applying coefficients thereto, wherein the algebraic sum of said coefficients substantially equals zero, to produce an output representative of the algebraic combination thereof;

second means coupled to the circuit means for receiving the outputs therefrom, raising at least some of said outputs to selected powers of said outputs, and for weighting said outputs by applying coefficients thereto, wherein the algebraic sum of said coefficients substantially equals zero, to produce an output representative of the algebraic combination thereof; and means coupled to the first and second means and responsive to said outputs therefrom for producing an output manifestation of the ratio of said outputs.

14. Apparatus for determining oxygen saturation of blood comprising:

source means for producing electro-magnetic radiation at first, second and third radiation wavelengths;

means coupled to the source means for supplying the radiation therefrom to blood under test with incident intensities at the respective wavelengths;

detector means disposed to receive radiation from the blood under test altered from the incident intensities of the respective wavelengths by the optical properties of the blood under test for producing signals representative of the intensities of the radiation received thereby at the respective wavelengths;

circuit means coupled to the detector means for producing a first output representative of the ratio of a first pair of the signals from said detector means, and for producing a second output representative of the ratio of a second pair of the signals from said detector means; and first means coupled to the circuit means for producing an output representative of the algebraic combination of selectively weighted first and second outputs;

second means coupled to the circuit means for producing an output representative of the algebraic combination of selectively weighted first and second outputs;

output means coupled to the first and second means and responsive to said outputs therefrom for producing an output manifestation of the ratio of said outputs of the first and second means; and the outputs of said circuit means being selectively weighted by amplifier gain and circuit component values of said first and second means to cause the partial derivative of said output manifestation of said output means with respect to the first output of said circuit means to be approximately zero near one extreme of the range of oxygen saturation to be measured, and to cause the partial derivative of the output manifestation of said output means with respect to the second output of said circuit means to be approximately zero near the other extreme of the range of values of oxygen saturation to be measured.

15. Apparatus for determining oxygen saturation of blood comprising:

source means producing electro-magnetic radiation at first, second and third radiation wavelengths;

means coupled to the source means for supplying the radiation therefrom to blood under test with incident intensities at the respective wavelengths;

detector means disposed to receive radiation from the blood under test altered from the incident intensities of the respective wavelengths by the optical properties of the blood under test for producing signals representative of the intensities of the radiation received thereby at the respective wavelengths;

circuit means coupled to the detector means for producing a first output representative of the ratio of a first pair of the signals from said detector means, and for producing a second output representative of the ratio of a second pair of the signals from said detector means;

the first, second and third wavelengths of the source means having values to cause the cumulative dependence of the ratio of resultant signals of a first pair of wavelengths as represented by the first output of said circuit means upon variations in physiologic parameters other than oxygen saturation to be minimized near one extreme of the range of values of oxygen saturation to be measured and to cause the cumulative dependence of the ratio of resultant signals at a second pair of wavelengths as represented by the second output of said circuit means upon variations in physiologic parameters other than oxygen saturation to be minimized near the other extreme of the range of values of oxygen saturation to be measured;

first means coupled to the circuit means for producing an output representative of the algebraic combination of selectively weighted first and second outputs;

second means coupled to the circuit means for producing an output representative of the algebraic combination of selectively weighted first and second outputs; and means coupled to the first and second means and responsive to said outputs therefrom for producing an output manifestation of the ratio of said outputs.

16. Apparatus for determining oxygen saturation of blood comprising:

source means for producing electro-magnetic radiation at first, second and third radiation wavelengths;

means coupled to the source means for supplying the radiation therefrom to blood under test with incident intensities at the respective wavelengths;

detecor means disposed to receive radiation from the blood under test altered from the incident intensities of the respective wavelengths by the optical properties of the blood under test for producing signals representative of the intensities of the radiation received thereby at the respective wavelengths;

circuit means coupled to the detector means for producing a first output representative of the ratio of a first pair of the signals from said detector means, and for producing a second output representative of the ratio of a second pair of the signals from said detector means; and first means coupled to the circuit means for producing an output representative of the algebraic combination of selectively weighted first and second outputs and square of one of the first and second outputs;

second means coupled to the circuit means for producing an output representative of the algebraic combination of selectively weighted first and second outputs and square of one of said first and second outputs;

means coupled to the first and second means and responsive to said outputs therefrom for producing an output manifestation of the ratio of said outputs; and the outputs of said circuit means being selectively weighted by amplifier gain and circuit component values of said first and second means to cause the partial derivative of said output manifestation of said output means with respect to the first output of said circuit means to be approximately zero near one extreme of the range of oxygen saturation to be measured, and to cause the partial derivative of the output manifestation of said output means with respect to the second output of said circuit means to be approximately zero near the other extreme of the range of values of oxygen saturation to be measured.

17. Apparatus for determining oxygen saturation of blood comprising:

source means for producing electro-magnetic radiation at first, second and third radiation wavelengths;

means coupled to the source means for supplying the radiation therefrom to blood under test with incident intensities at the respective wavelengths;

detector means disposed to receive radiation from the blood under test altered from the incident intensities of the respective wavelengths by the optical properties of the blood under test for producing signals representative of the intensities of the radiation received thereby at the respective wavelengths;

circuit means coupled to the detector means for producing a first output representative of the ratio of a first pair of the signals from said detector means, and for producing a second output representative of the ratio of a second pair of the signals from said detector means;

the first, second and third wavelengths of the souce means having values to cause the cumulative dependence of the ratio of resultant signals of a first pair of wavelengths as represented by the first output of said circuit means upon variations in physiologic parameters other than oxygen saturation to be minimized near one extreme of the range of values of oxygen saturation to be measured and to cause the cumulative dependence of the ratio of resultant signals at a second pair of wavelengths as represented by the second output of said circuit means upon variations in physiologic parameters other than oxygen saturation to be minimized near the other extreme of the range of values of oxygen saturation to be measured;

first means coupled to the circuit means for producing an output representative of the algebraic combination of selectively weighted first and second outputs and square of one of the first and second outputs;

second means coupled to the circuit means for producing an output representative of the algebraic combination of selectively weighted first and second outputs and square of one of said first and second outputs; and means coupled to the first and second means and responsive to said outputs therefrom for producing an output manifestation of the ratio of said outputs.

18. Apparatus for determining oxygen saturation of blood comprising:

source means for producing electro-magnetic radiation at a plurality of radiation wavelengths;

means coupled to the source means for supplying the radiation therefrom to blood under test with incident intensities and the respective wavelengths;

detector means disposed to receive radiation from the blood under test altered from the incident intensities of the respective wavelengths by the optical properties of the blood under test for producing signals representative of the intensities of the radiation received thereby at the respective wavelengths;

circuit means coupled to the detector means for producing a plurality of outputs each representative of the ratio of a respective pair of the signals from said detector means;

first means coupled to the circuit means for producing corresponding resultant signals from at least one output multiplied in value by an output a selected number of times and for producing an output representative of the sum of all selectively weighted resultant signals; and second means coupled to the circuit means for producing corresponding resultant signals for at least one output multiplied in value by an output a selected number of times and for producing an output representative of the sum of all selectively weighted resultant signals;

means coupled to the first and second means and responsive to said outputs therefrom for producing an output manifestation of the ratio of said outputs; and the outputs of said circuit means being selectively weighted by amplifier gain and circuit component values of said first and second means to cause the partial derivative of said output manifestation of said output means with respect to the first output of said circuit means to be approximately zero near one extreme of the range of oxygen saturation to be measured, and to cause the partial derivative of the output manifestation of said output means with respect to the second output of said circuit means to be approximately zero near the other extreme of the range of values of oxygen saturation to be measured.

19. Apparatus for determining oxygen saturation of blood comprising:

source means for producing electro-magnetic radiation at a plurality of radiation wavelengths;

means coupled to the source means for supplying the radiation therefrom to blood under test with incident intensities at the respective wavelengths;

detector means disposed to receive radiation from the blood under test altered from the incident intensities of the respective wavelengths by the optical properties of the blood under test for producing signals representative of the intensities of the radiation received thereby at the respective wavelengths;

circuit means coupled to the detector means for producing a plurality of outputs each representative of the ratio of a respective pair of the signals from said detector means;

the radiation wavelengths of said source means being selected to cause the cumulative dependence of the ratios of resultant signals of respective pairs of wavelengths, represented by respective outputs of said circuit means, upon variations in physiologic parameters other than oxygen saturation to be minimized near respective different values in the range of values of oxygen saturation to be measured;

first means coupled to the circuit means for producing corresponding resultant signals from at least one output multiplied in value by an output a selected number of times and for producing an output representative of the sum of all selectively weighted resultant signals; and means coupled to the first means and responsive to said output therefrom for producing an output manifestation of oxygen saturation.

* * * * *

UNITED STATES PATENT AND TRADEMARK OFFICE
CERTIFICATE OF CORRECTION

PATENT NO. : 4,114,604
DATED : September 19, 1978
INVENTOR(S) : Robert F. Shaw and John M. Sperinde It is certified that error appears in the above—identified patent and that said Letters Patent are hereby corrected as shown below:

ON THE FRONT PAGE OF THE PATENT:

Add: Assignee: OXIMETRIX, INC., Mountain View, California

Signed and Sealed this

Tenth Day of April 1979

[SEAL]

Attest:

RUTH C. MASON
Attesting Officer

DONALD W. BANNER
Commissioner of Patents and Trademarks